United States Patent [19]

Wrighton et al.

[11] Patent Number: 5,223,117
[45] Date of Patent: Jun. 29, 1993

[54] TWO-TERMINAL VOLTAMMETRIC MICROSENSORS

[75] Inventors: Mark S. Wrighton, Winchester, Mass.; James J. Hickman, Falls Church, Va.; Paul E. Laibinis, Plains, Pa.; David Ofer, Newton, Mass.; Chad A. Mirkin, Skokie, Ill.; James R. Valentine, Medford; George M. Whitesides, Newton, both of Mass.

[73] Assignees: Mass. Institute of Technology; Pres. & Fellows of Harvard College, both of Cambridge, Mass.

[21] Appl. No.: 695,254

[22] Filed: May 3, 1991

[51] Int. Cl.$^5$ .............................................. G01N 27/26
[52] U.S. Cl. ................................... 204/415; 204/416; 204/418; 204/431; 204/433; 204/435
[58] Field of Search ............... 204/415, 416, 418, 419, 204/431, 433, 435

[56] References Cited

U.S. PATENT DOCUMENTS

| | | | |
|---|---|---|---|
| 4,545,382 | 10/1985 | Higgins et al. | 204/415 |
| 4,717,673 | 1/1988 | Wrighton et al. | 436/68 |
| 4,895,705 | 1/1990 | Wrighton et al. | 422/68 |
| 4,929,313 | 5/1990 | Wrighton | 204/433 |
| 4,936,956 | 6/1990 | Wrighton et al. | 204/153.21 |

OTHER PUBLICATIONS

Hammond, et al. "Synthesis, N.m.r. Spectra, and Structure of Macrocyclic Compounds Containing the Ferrocene Unit" *J. Chem. Soc. Perkins Trans.* I 707–715 (1983).

Medina, et al, "Ferrocenyldimethyl-[2.2]-cryptand: Solid State Structure of the External Hydrate and Alkali and Alkaline-earth-dependent Electrochemical Behaviour" *J. Chem. Soc. Chem. Commun.* 290–292 (1991).

Shu, et al, "Synthesis and Charge-Transport Properties of Polymers Derived from the Oxidation of 1-Hydro-1-'-(6-(pyrrol-1-yl)hexyl)-4,4'-bipyridinium Bis(hexafluorophosphate) and Demonstration of a pH-Sensitive Microelectrochemical Transistor Derived from the Redox Properties of a Conventional Redox Center" *J. Phys. Chem.* 92:5221–5229 (1988).

Nuzzo, et al. "Adsorption of Bifunctional Organic Disulfides on Gold Surfaces" *J. Am. Chem. Soc.* 105:4481–4483 (1983).

Brown, et al. "Illustrative Electrochemical Behavior of Reactants Irreversibly Adsorbed on Graphite Electrode Surfaces" *J. Electroanal. Chem.* 72:379–387 (1976).

Bain, et al. "Depth Sensitivity of Wetting: Monolayers of $\omega$-Mercapto Ethers on Gold" *J. Am. Chem. Soc.* 110:5897–5898 (1988).

Fackler and Porter "Gold Rings That Do Not Glister. The Crystal and Molecular Structures of Two Novel Gold (II) Compounds Containing 12- and 13-Atom Gold-Sulfur Rings, $[Au(CH_2)_2P(C_6H_5)_2]_2S_8$ and $[Au(CH_2)_2P(C_6H_5)_2]_2S_9$" *J. Am. Chem. Soc.* 108:2750–2751 (1986).

(List continued on next page.)

Primary Examiner—John Niebling
Assistant Examiner—Bruce F. Bell
Attorney, Agent, or Firm—Kilpatrick & Cody

[57] ABSTRACT

Self-assembly of a chemically insensitive redox material, such as ferrocenyl thiol, and a chemically sensitive redox material, such as a quinone thiol, onto microelectrodes forms the basis for a two-terminal, voltammetric microsensor having reference and sensor functions on the same electrode. Detection is based on measuring the potential difference of current peaks for oxidation and reduction of the reference (ferrocene) and indicator (quinone) in aqueous electrolyte in a two-terminal, linear sweep voltammogram using a counterelectrode of relatively large surface area. Use of microelectrodes modified with monolayer coverages of reference and indicator molecules minimizes the size of the counterelectrode and the perturbation of the solution interrogated. Key advantages are that the sensor requires no separate reference electrode and the sensor functions as long as current peaks can be located for reference and indicator molecules.

14 Claims, 6 Drawing Sheets

OTHER PUBLICATIONS

Bain, et al. "Molecular-Level Control over Surface Order in Self-Assembled Monolayer Films of Thiols on Gold" *Science* 240:62-63 (1988).

Bain, et al. "Correlations between Wettability and Structure in Monolayers of Alkanethiols Adsorbed on Gold" *J. Am. Chem. Soc.* 110:3665-3668 (1988).

Bain, et al. "Formation of Two-Component Surfaces by the Spontaneous Assembly of Monolayers on Gold from Solutions Containing Mixtures of Organic Thiols" *J. Am. Chem. Soc.* 110:6560-6561 (1988).

Bain, et al. "Modeling Organic Surfaces with Self-Assembled Monolayers" *Angew. Chem.* 28:506-512.

Whitesides, et al. "Wet Chemical Approaches to the Characterization of Organic Surfaces: Self-Assembled Monolayers, Wetting, and the Physical-Organic Chemistry of the Solid-Liquid Interface" *Langmuir* 6:87-96 (1990).

Bain, et al. "Formation of Monolayer Films by the Spontaneous Assembly of Organic Thiols from Solution onto Gold" *J. Am. Chem. Soc.* 111:321-335 (1989).

Allara, et al. "Spontaneously Organized Molecular Assemblies. 1. Formation, Dynamics, and Physical Properties of $\eta$-Alkanoic Acids Adsorbed from Solution on an Oxidized Aluminum Surface" *Langmuir* 1:45-52 (1985).

Stern, et al. "Adsorbed Thiophenol and Related Compounds Studied at Pt(111) Electrodes by EELS, Auger Spectroscopy, and Cyclic Voltammetry" *J. Am. Chem. Soc.* 110:4885-4893 (1988).

Hubbard "Electrochemistry at Well-Characterized Surfaces" *Chem. Rev.* 88:633-656 (1988).

Chidsey, et al. "Coadsorption of Ferrocene-Terminated and Unsubstituted Alkanethiols on Gold: Electroactive Self-Assembled Monolayers" *J. Am. Chem. Soc.* 112:4301-4306.

Blackburn, et al. "The Suspended Mesh Ion Selective Field Effect Transistor" *J. Electrochem. Soc.* 129(11):2580-2584 (1982).

Haemmeril, et al. "Ion-Selective Electrode for Intracellular Potassium Measurements" *Anal. Chem.* 52:1179-1182 (1980).

Murray "Chemically Modified Electrodes" *Electroanalytical Chemistry* vol. 13 edited by A. J. Bard (Marcel Dekker, N.Y. 1984).

Janata, et al. "Ion-sensitive Field Effect Transistors" *Ion-Selective Electrode Rev.* 1:31-79 (1979).

Chemical Abstracts, vol. 99, Abstract No. 204571r (1983).

Jpn Kokai Tokkyo Koho JP 58,114,465 Rubinstein "Voltammetric pH Measurements with Surface-Modified Electrodes and a Voltammetric Internal Reference" *Analy. Chem.* 56:1135 (1984).

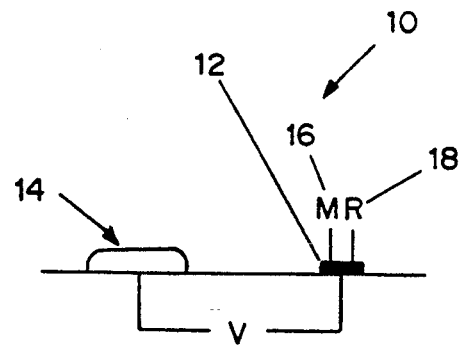
FIGURE 1a
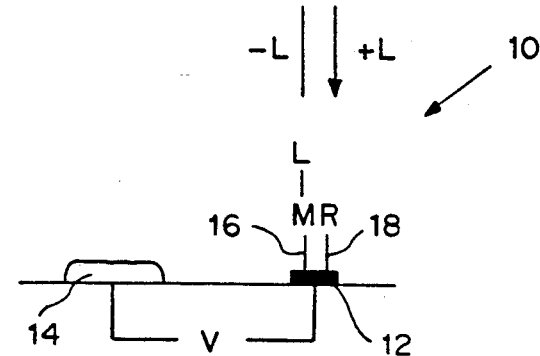
FIGURE 1b
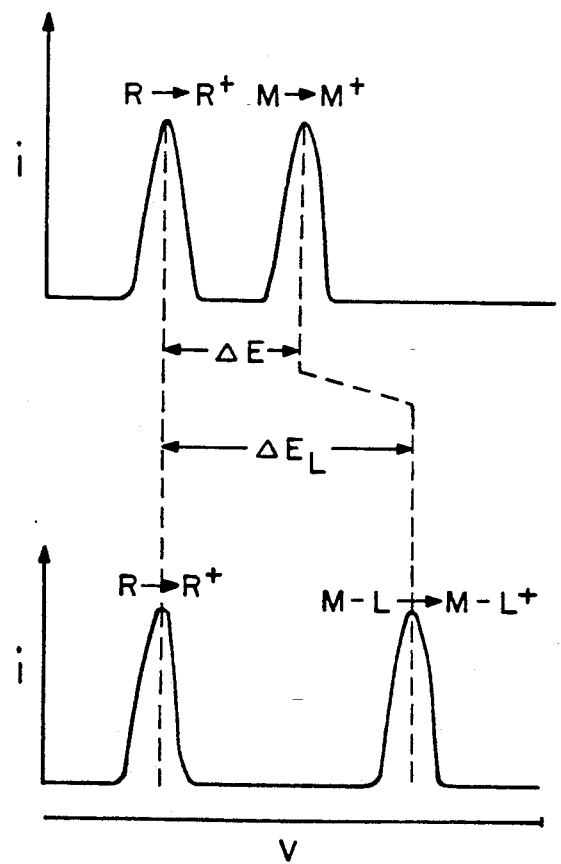

TWO-TERMINAL VOLTAMMETRIC MICROSENSORS

BACKGROUND OF THE INVENTION

The United States government has rights in this invention by virtue of grants from the Office of Naval Research and the Defense Advanced Research Projects Agency.

This invention is in the general area of microelectrochemical devices and is specifically a two-terminal, voltammetric microsensor.

There is an ongoing need to provide stable, microelectrochemical sensor analogous to and integrable with traditional silicon wafer technology. Devices of this sort have been described, for example, in U.S. Pat. No. 4,895,705, U.S. Pat. No. 4,717,673 and U.S. Pat. No. 4,936,956 to Wrighton, et al., the teachings of which are specifically incorporated herein.

These devices still require separate reference and indicator electrodes in order to produce reproducible results.

It is therefore an object of the present invention to provide microelectrochemical sensors having both the indicator(s) and reference functions located on the same microelectrode.

It is a further object of the present invention to provide methods for making and using microelectrochemical sensors having both the indicator(s) and reference functions located on the same microelectrode.

SUMMARY OF THE INVENTION

A voltammetric sensing system is prepared as a two terminal device with surface-confined, internal, chemically insensitive, redox reagent-based reference and chemically sensitive redox reagent-based indicator, having a voltammetric response as a function of chemical concentration. The preferred embodiment is a two-terminal voltammetric microsensor with an internal reference consisting of two electrodes: a counter electrode which is significantly larger in area than the working electrode, and a working electrode which is derivatized with at least two, surface-confined, reversibly electroactive, redox reagents, one reagent having an electrochemical response that is insensitive to the medium and that serves as a reference, and the other reagent(s) having electrochemical response(s) sensitive to analyte(s), serving as indicators(s) for the analyte(s). The working electrode may consist of more than one microelectrode, if they are shorted together and operated as one terminal of the two terminal device.

Current at the working electrode is recorded as its potential is swept versus that of the counter electrode in a two-terminal linear sweep voltammogram. If the counter electrode is large relative to the microelectrode, its potential does not change. The counter electrode area must be at least $10^2$ to $10^3$ times the working electrode area, depending on the accuracy of voltammetric detection desired. The area must be even larger if the working electrode has greater than monolayer coverage of electroactive material. Sensing is accomplished by measuring the potential difference(s) between the current peak(s) for the indicator reagent(s) and that for the reference reagent.

The key advantages of the device are that the sensor requires no separate reference electrode and that it functions as long as current peaks for the reference and indicator reagents can be detected. The device can be utilized in a variety of sensing applications, including in vivo biomedical sensing. The small size of the working electrode with internal reference makes it minimally invasive and an external patch electrode can be used as the counter electrode. Other applications include sensing of industrial gases, sensing of anaesthetic gases, sensing in wastewater streams, and air pollution monitoring.

A pH sensor is described in detail, using ferrocenyl and quinone thiols bound to a gold electrode as the reference and sensing reagents, respectively. This device measures acidity at very high acid concentrations. A CO sensor is also described, using ferrocenyl thiol and a ferrocenyl ferraazetine disulfide bound to a gold microelectrode surface as the reference and sensing reagents, respectively. This device measures accumulated exposure to CO.

BRIEF DESCRIPTION OF THE DRAWINGS

FIG. 1A illustrates cross-sectional views of a two-terminal, voltammemtric microsensor showing idealized response to a species L which binds to the indicator molecule M. FIG. 1B are linear sweep voltammograms that reveal a difference between the current peak for oxidizing the reference molecule, R, relative to that for M or M-L, depending on the presence of L.

DETAILED DESCRIPTION OF THE INVENTION

Figure 2:
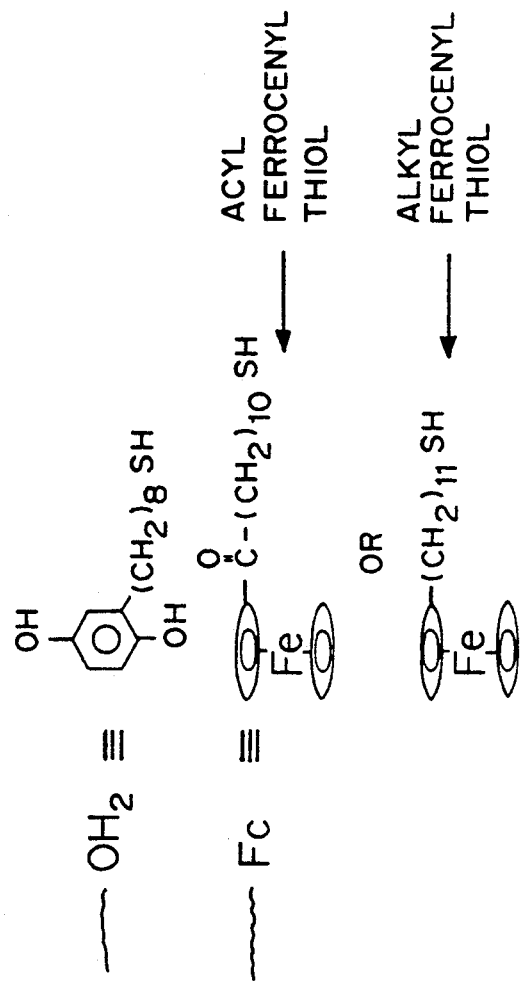
FIG. 2 illustrates a cross-sectional view of a two-terminal, voltammetric microsensor based on the self-assembly of a ferrocenyl thiol and a quinone thiol serving as reference and indicator, respectively.
Figure 2:
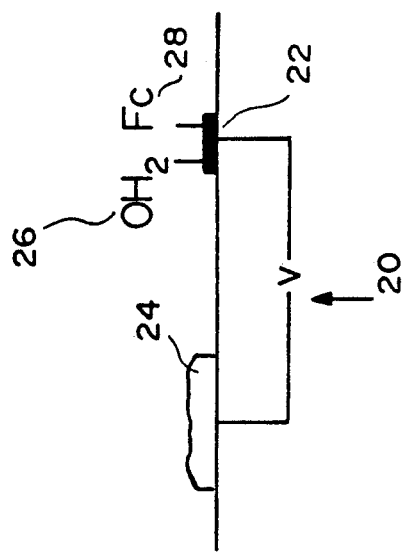

The two-terminal, voltammetric microsensor is formed of two components:

(1) a microelectrode (referred to herein as the working electrode) having at least one chemically sensitive redox material and a chemically insensitive redox material located thereon; and (2) a larger counterelectrode.

The redox materials are characterized as "surface confined", i.e., in electrical contact with the microelectrode, whether in a liquid electrolyte or in a solid state electrolyte.

As shown schematically in FIG. 1, the sensor 10 consists of a working microelectrode 12 and a counterelectrode 14, with two redox active materials 16 and 18 for detecting a chemical species L, where the indicator material 16 is sensitive to the presence of L and the reference material 18 is not. As shown in FIGS. 1B, interaction of L with the indicator material 16 alters the difference in redox potential measured between the indicator 16 and the reference 18.

Detection is accomplished by measuring the potential difference, delta E, associated with current peaks for oxidation (or reduction) of microelectrode-confined redox reagents, where the magnitude of delta E can be related to the concentration of analyte. One of the electrode-bound reagents has an electrochemical response that is insensitive to variations in the medium and serves as the reference. At least one of the electrode-bound reagents is chemically sensitive and serves as the indicator. Current peaks for oxidation or reduction of the reference and indicator are determined from two-terminal, linear sweep voltammograms using a counterelectrode having an area much larger than the sensor electrode.

The key advantage of the device is that it does not require a reference electrode, since the indicator and reference molecules are both on the sensor electrode. A second advantage is that the sensor function is based on peak-to-peak separations, delta E, rather than on peak amplitudes. Accordingly, the sensor can be useful as long as peaks can be located, even when slow decomposition of the electrode-bound reagents occurs.

The Counterelectrode

A relatively large surface area counterelectrode is needed so that the linear sweep of applied voltage yields only a change in potential of the sensor electrode. For example, for a working microelectrode with about one monolayer of redox active material, the counterelectrode is $10^3$ times larger than the sensor electrode the counterelectrode will move only approximately 1 mV upon application of a one volt potential difference.

The counter electrode area should be at least $10^2$ to $10^3$ times the working electrode area for a working electrode with about one monolayer electroactive material, and for coverages of redox reagents above monolayer levels the counter electrode size should scale approximately linearly with the number of monolayers of electroactive material on the working electrode:

counter electrode area = [(> $10^2$ – $10^3$) (working electrode area)] × [number of monolayers of redox material]

For biomedical applications the counter electrode can be a transdermal patch electrode. All that is required in any application is that it be sufficiently large, and that it be made of a material which is chemically inert to the medium so that its potential does not change significantly during the course of measurement. Suitable materials in many applications include platinum and gold, and, slightly less versatile, stainless steel and carbon.

The Working Microeleotrode

The selection criteria for use as reference and indicator reagents on the working electrode are:

1. Reversible redox activity with well-defined cyclic voltammetry oxidation and/or reduction peaks. Examples include:

a) redox molecules and material with molecule-based redox processes: e.g., ferrocenes, polyvinyl ferrocene, quinone, viologen, polyviologen, polyviologen-quinone, polycation charge compensated with electroactive metal complex (polyvinylpyridine $H^+M^-$).

b) inorganic materials and metal oxides: e.g. Prussian Blue, $Ni(OH)_2$, $RuO_x$.

Type a) redox reagents having molecular redox properties are generally preferable because they tend to exhibit the highest degree of Nernstian electrochemical reversibility bu other types of materials, such as those discussed above, can be used.

2. One redox reagent, the reference, must have a redox potential which is insensitive to the chemical medium. Examples include ferrocenyl thiol, polyvinylferrocene, viologen, polyviologen, and polythiophene.

What qualifies as a suitable reference redox reagent can vary from application to application or medium to medium.

Figure 3A:
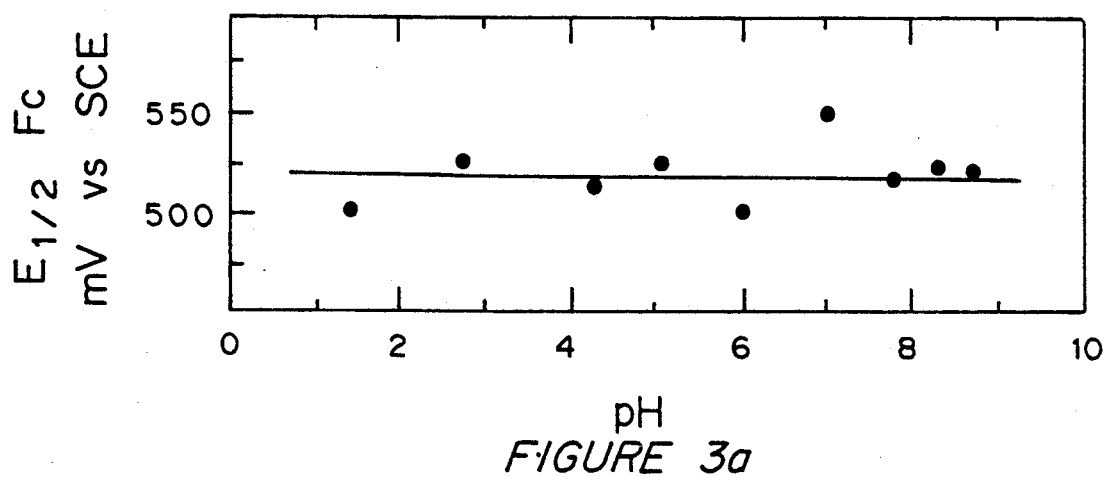
FIG. 3 is a graph of $E_{\frac{1}{2}}$ versus SCE for the surface-confined ferrocene thiol as a function of pH (FIG. 3A) and a graph of the difference between cathodic peak potentials for surface-confined acyl ferrocenium and quinone as a function of pH from two-terminal, voltammetric scans (FIG. 3B). All data are from voltammograms recorded at 500 mV/s in 1.0 M $NaClO_4$ in buffered solution.
Figure 3B:
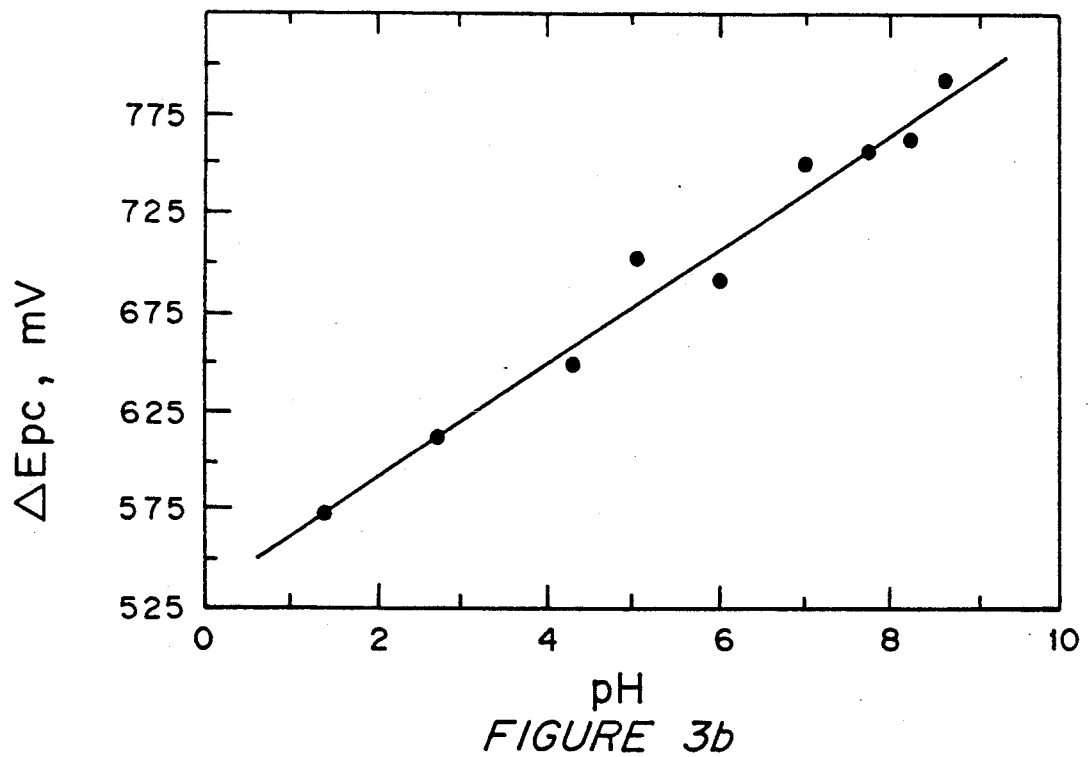
Figure 4A:
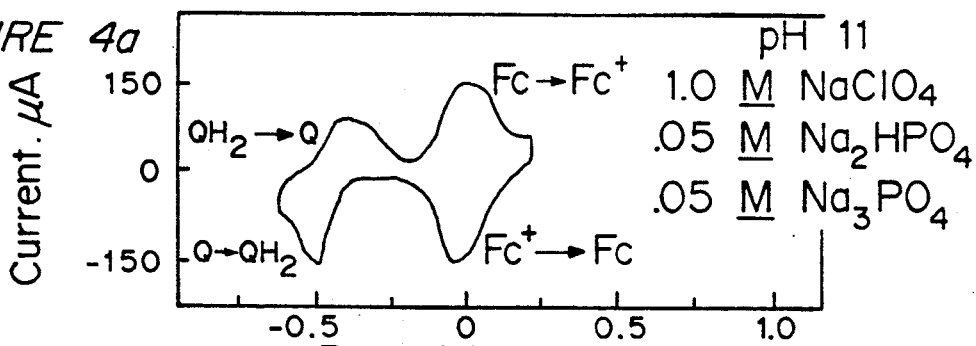
FIG. 4a–4d show the cyclic voltammetry (500 mV/s) for a Au macroelectrode derivatized with alkyl ferrocene thiol and quinone thiol in buffers, from top to bottom: 1.0 M $NaClO_4$ buffered to pH 11 with phosphate; 0.1 M $CHClO_4$; 1.0 M $HClO_4$; 10 M $HClO_4$. The reference is the average position of the oxidation and reduction waves for the ferrocene system.
Figure 4B:
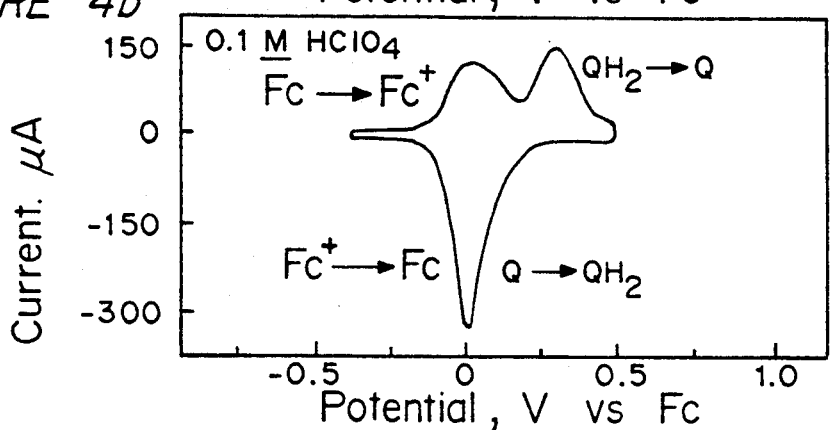
Figure 4C:
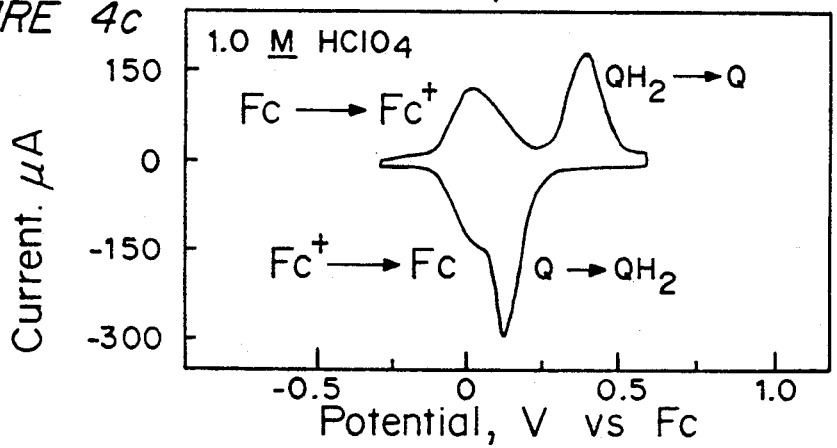
Figure 4D:
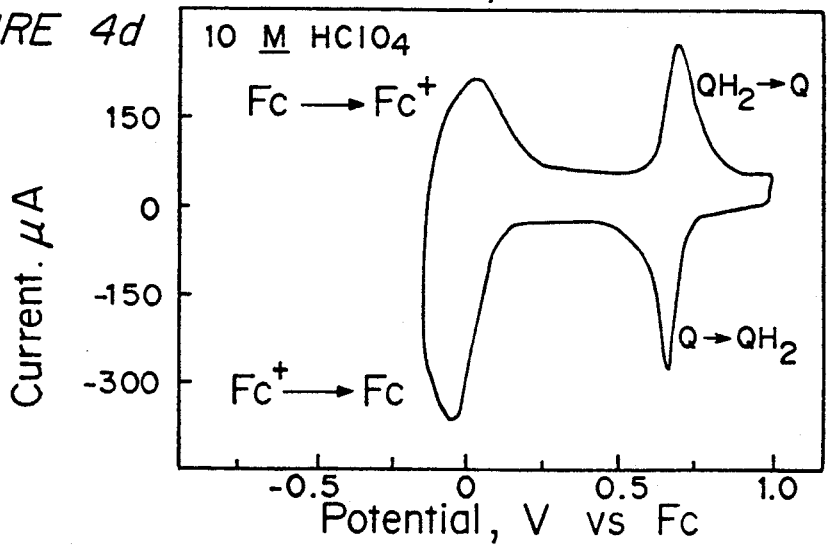

3. The other one or more redox reagent(s) must have redox potential(s) sensitive to the analyte. Examples include:

pH sensitive: quinone thiol (as shown in FIGS. 3 and 4); monoquaternized N-alkyl-4,4'-bipyridinium, RuO., and $Ni(OH)_2$.

CO sensitive: ferrocenyl ferraazetine disulfide (as shown in FIG. 3);

alkaline metal cation sensitive: 1,1'-(1,4,10,13-tetraoxa-7,16-diazacyclooctadecane-7,16-diyl dimethyl), ferrocenyl thiol, and other ferrocene derivatives containing covalently attached cryptands. These materials are described, for example, Hammond, et al., *J. Chem. Soc. Perkin. Trans. I* 707 (1983); Medina, et al., *J. Chem. Soc. Chem. Commun.* 290 (1991); Shu and Wrighton, *J. Phys. Chem.* 92, 5221 (1988). Included are examples such as the above ferrocenyl ferraazetine and ferrocenyl cryptand, in which an ordinarily chemically insensitive redox center (ferrocene) is covalently linked to a chemical recognition site in such a way as to make its's redox potential chemically sensitive. Also suitable are molecules or polymers in which the sensor and reference functionalities are covalently linked such as 1-hydro-1'-(6-(pyrrol-1-yl)hexyl)-4,4'-bipyridinium bis(hexafluorophosphate), as described by Shu and Wrighton, *J. Phys. Chem.* 92, 5221 (1988).

4. The redox reagents must be durably surface confinable. Examples include:

a) spontaneously self-assembling (adsorbing to the working electrode) molecules: ferrocenyl thiols, quinone thiol, ferrocenyl isonitriles, porphyrinyl isonitrile, ferrocenyl ferraazetine disulfide, ferrocenyl dithiocarbamates, on gold or platinum; ferrocenyl carboxylates on indium tin oxide.

Self-assembling reagents are preferred because they automatically yield single monolayers and it is easy to mix sensor and reference reagents on single microelectrodes.

b) electrodeposited redox reagents. This includes most of the electroactive polymers mentioned previously such as polyvinylferrocene, polyvinylpyridine $H^+M^-$, polythiophene.

Here it can be advantageous to use two or more independently addressable microelectrodes because it can be difficult to confine the reference and indicator reagents to the same microelectrode. All the microelectrodes can then be shorted together and operated as a single working microelectrode.

The preferred polymers are those that can be electrochemically deposited on individual microelectrodes with precision, polymerized, as respond to a signal in a reversible manner, in a way that can be electrochemically detected. Other such materials are described by R. W. Murray in *Electroanalytical Chemistry*, vol. 13, edited by A. J. Bard (Marcel Dekker, NY 1984), the teachings of which are specifically incorporated herein.

In the preferred embodiment, these materials are applied to electrically conductive microelectrodes having good stability and ability to be functionalized, such as platinum, gold, silver, palladium, and combinations thereof. Use of microelectrodes modified with monolayer coverages of reference and indicator molecules minimizes the size of the counterelectrode and the perturbation of the solution interrogated. It should be clear that monolayer redox reagents and microelectrodes are not required, but their use has the advantage that very small amounts of charge are involved in detection.

The microelectrodes themselves can, for example, be made by conventional microfabrication techniques and consist of electrically conductive materials deposited on silicon substrates, the material having good adhesion to the substrate, good stability, and ability to be functionalized. Platinum or gold are optimal materials. Methods for applying these materials are well known to those skilled in the art of silicon wafer processing technology.

A typical microelectrode array consists of eight individually addressable microelectrodes, each 100 $\mu$m long $\times$ 2.5 2.5 $\mu$m wide $\times$ 0.1 $\mu$m thick, separated from each other by 1.5 $\mu$m, with leads to the microelectrodes from macroscopic bonding pads, all on a 3 mm $\times$ 3 mm $\times$ 3 mm Si chip with insulating layers of $SiO_2$ and $SI_3N_4$ between the Si and the microelectrodes. For purposes of making solid-state two-terminal voltammetric sensors capable of sensing gases, a large counter electrode is also fabricated on the Si chip or a spot of silver epoxy is also applied to the chip for use as the counter electrode, and following derivatization of the working microelectrode with reference and sensor redox reagents, a solid electrolyte such as poly(vinyl alcohol)/$H_3PO_4$ is coated onto the device, thereby providing an ionic conductor to close the electrochemical circuit between the counter and working electrodes while at the same time allowing exposure of the working electrode to ambient atmosphere. Of, for example, the microelectrode can consist of a metallic microwire (e.g., platinum, 25 $\mu$m diameter) sealed in a glass capillary at one end and electrically contacted at the other end. The sealed end is then polished to reveal a microdisc (25 $\mu$m diameter) electrode. This technique is particularly well suited to in vivo biomedical sensing where the sharp microelectrode tip can be introduced as a hypodermic. These are most preferred type of microelectrodes for use as working electrodes, but, depending on the application, and on the constraints it might impose on size and/or shape of the working electrode, any electrode which has the desired stability, to which redox sensor and reference reagents can be durably confined, and which is sufficiently smaller than the counter electrode, will be adequate as working electrode.

The self-assembly of thiol reagents provides a reproducible method, applicable to many chemical functionalities, as described, for example, by R. G. Nuzzo and D. L. Allara, *J. Am. Chem. Soc.* 105, 4481 (1983); A. P. Brown, C. Koval, and F. C. Anson, *J. Electroanal. Chem.* 72, 379 (1976); C. D. Bain and G. M. Whitesides, *J. Am. Chem. Soc.* 110, 5897 (1988); M. D. Porter, et al., *J. Am. Chem. Soc.* 108, 3559 (1986); C. D. Bain and G. M. Whitesides, *Science* 240, 62 (1988); *J. Am. Chem. Soc.* 110, 3665, 6561 (1988); *Agnew. Chem.* 101, 522 (1989); G. M. Whitesides and P. E. Laibinis, *Langmuir* 6, 87 (1990); C. D. Bain et al., *J. Am. Chem. Soc.* 111, 321 (1989); D. L. Allara and R. G. Nuzzo, *Langmuir* 1, 45, 52 (1985): D. A. Stern, et al., *J. Am. Chem. Soc.* 110, 4885 (1988); A. T. Hubbard, *Chem. Rev.* 88, 633 (1988); and C. E. D. Chidsey, et al., *J. Am. Chem. Soc.* 112, 4301 (1990); the teachings of which are specifically incorporated herein, for assembly for device-active materials, but there are a large number of other electrode modification techniques that can be useful, as described, for example, by R. W. Murray in *Electroanalytical Chemistry*, A. J. Bard, Ed., Vol 13, p 191 (Dekker, New York, 1984), and references therein.

For example, a sensor capable of detecting a change in pH is based on measuring the potential difference of current peaks for oxidation and reduction of a reference formed of ferrocene and an indicator formed of a quinone in aqueous electrolyte in a two-terminal, linear sweep voltammogram using a counterelectrode of relatively large surface area. The ferrocene center has an $E_{\frac{1}{2}}$ value that is insensitive to pH, while that of the quinone is pH sensitive. Thus, the ferrocene center serves as the reference and the quinone as the indicator for pH.

The sensor can as easily utilize other indicator molecules. For example, the polymers can be derivatized with reagents such as biologically active agents, including enzymes and ionophores that complex with ions such as lithium and calcium. Elemental ions such as platinum can also be bound to or embedded into the polymer, as well as enzymes such as hydrogenases which can be used to equilibrate the redox polymer with the enzyme substrates.

EXAMPLE 1:

Construction of a Surface Confined, Two-terminal pH Sensor.

Self-assembly of a ferrocenyl thiol and a quinone thiol onto gold (Au) microelectrodes was used to demonstrate the manufacture of a two-terminal, voltammetric microsensor having reference and sensor functions on the same electrode for use as a pH sensor.

Two redox active molecules were self-assembled on Au microelectrodes by adsorption of the RSH group on gold (as thiolate, $RS^-Au^+$), as described, for example, by Nuzzo and Allara, *J. Am. Chem. Soc.* 105, 4481 (1983); Brown, et al., *J. Electroanal. Chem.* 72, 379 (1976); Bain and Whitesides, *J. Am. Chem. Soc.* 110, 5897 (1988); and Porter, et al., *J. Am. Chem. Soc.* 108, 3559 (1986), and as shown schematically in FIG. 2.

The reference molecule 28 is a ferrocene (Fc), a redox center having a chemically insensitive formal potential.[6] The indicator molecule 26 is a hydroquinone ($QH_2$) having a pH-dependent redox potential, described in "Introduction to Organic Chemistry", pp. 1014–1020, Streitwieser and Heathcock, 2nd edition (McMillan, New York 1981).

Au microelectrodes (approximately $10^3$ $\mu m^2$) or Au macroelectrodes (approximately 1 $cm^2$) can be modified with $QH_2$ or Fc by dipping the Au into solutions containing one or both of the thiol reagents. Preparation of 2-(8-mercapto-octyl)hydroquinone involves several steps: 1,4-dimethoxy-benzene was deprotonated with n-butyllithium and added to excess 1,8-dibromo-octane; vacuum distillation afforded 2-(8-bromo-octyl)-1,4-dimethoxybenzene; demethylation was accomplished in quantitative yield with $BBr_3$; the bromide was displaced by thioacetate; and subsequent hydrolysis under acidic conditions yields the thiol which was purified by chromatography. Materials were characterized by $^1H$ NMR spectroscopy. Anal. Calcd (Found) for $C_{14}H_{22}O_2S$: C, 66.10 (66.21); H, 8.72 (8.58); S, 12.60 (12.57). The molecules self-assemble onto the Au surfaces when the Au is placed into approximately 1 mM solution of Fc or $QH_2$ in tetrahydrofuran (THF) or ethanol:hexane, 1:1. Mixtures of Fc and $QH_2$ self-assemble onto Au from a $QH_2$:Fc, 2:1 mixture in THF or in ethanol:hexane, 1:1, at a total thiol concentration of approximately 1 mM. All derivatizations were carried out under argon at 25° C. for approximately 24 hr.

Cyclic voltammograms for Au macroelectrodes modified with pure Fc, $QH_2$, or a combination of Fc and $QH_2$, show a persistent and consistent electrochemical response with about one monolayer of redox active molecules. Coverages determined from integration of the current-voltage curves are between 3 to $5 \times 10^{-10}$ mol/$cm^2$. The combination of $QH_2$ and Fc on the Au yields an electrochemical response expected from the presence of both redox systems.

EXAMPLE 2:

Use of the Two-terminal Voltammetric Sensor as a pH Sensor.

The electrochemical response for a Au microelectrode derivatized with $QH_2$ (acyl ferrocene thiol) and Fc (quinone thiol) was measured by cyclic voltammetry at 500 mV/s at three values of pH, 1.4, 4.3 and 6.0, using as the base electrolyte 1.0 M $NaCLO_4$, and phosphate, acetate, and phosphate buffers, respectively. The result indicates that the redox potential for the $Fc^+/Fc$ system, equation (1), is pH insensitive, whereas the redox response for the $Q/QH_2$ system, equation (2), depends on pH.

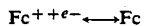
$$Fc^+ + e^- \longleftrightarrow Fc \quad (1)$$

$$Q + 2e^- + 2H^+ \longleftrightarrow QH_2 \quad (2)$$

When the Au microelectrode is run as the sensor electrode in a two-terminal device (approximately 1 $cm^2$ Pt counterelectrode), the voltammograms are superimposable on the curves obtained using a saturated calomel (SCE) reference electrode.

The microelectrodes show a somewhat smaller potential window than macroelectrodes in the aqueous electrolytes. This disadvantage is, however, compensated for by the fact that microelectrodes modified with a monolayer of reference and indicator molecules minimize the charge passed in effecting the movement of potential of the sensor electrode. Thus, both the size of the counterelectrode and the perturbation of the solution interrogated can be minimized.

The surface-confined $Fc^+/Fc$ system behaves ideally at all values of pH investigated (0–10). The surface-confined $Q/QH_2$ system is not ideal, in that there is a large difference in the potential for the anodic and cathodic current peaks. Despite the non-ideality, the effect of pH on the electrochemical response of $Q/QH_2$ is reproducible. Both the anodic and cathodic current peaks for the quinone system shift to more positive potentials at lower pH. FIG. 3 shows the lack of an effect of pH on $E_{\frac{1}{2}}$ of the surface-confined $Fc^+/Fc$ system and also shows the pH dependence of the potential difference between the cathodic current peaks, delta $E_{pc}$, for the processes shown in equations (1) and (2). The linear response to the solution pH forms the basis for a pH sensor system where the $Fc^+/Fc$ serves as the reference and the $Q/QH_2$ serves as the indicator.

EXAMPLE 3:

Stability of Two-terminal Sensor in Chemical Media.

Cyclic voltammetry at 500 mV/s for a Au macroelectrode derivatized with alkyl ferrocene thiol and quinone thiol in 1.0 M $NaClO_4$ buffered to pH 11 with phosphate; 0.1 M $HClO_4$; 1.0 M $HCLO_4$; and 10 M $HClO_4$, is shown in FIGS. 4a–4d. The reference is taken to be the average position of the oxidation and reduction waves for the ferrocene system. The results illustrate the electrochemical response in aqueous media containing different concentrations of $HClO_4$. The electrochemical response of the redox molecules persists even in 10 M $HClO_4$. The response for the $Q/QH_2$ system moves from approximately 0.5 V negative (pH=11) of the ferrocene to approximately 0.5 V positive (10 M $HClO_4$) of ferrocene for the media used. Measuring $H^+$ activity in highly acidic media is thus possible with the $Q/Fc(CH_2)$ SH-modified electrode. In applications, locating peak positions in linear sweep voltammetry can be improved by using derivative voltammetry to locate the peaks, as described by Parker in *Electroanalytical Chemistry*, Bard, editor, vol. 14, p.1 (Dekker, NY 1986).

Figure 5A:
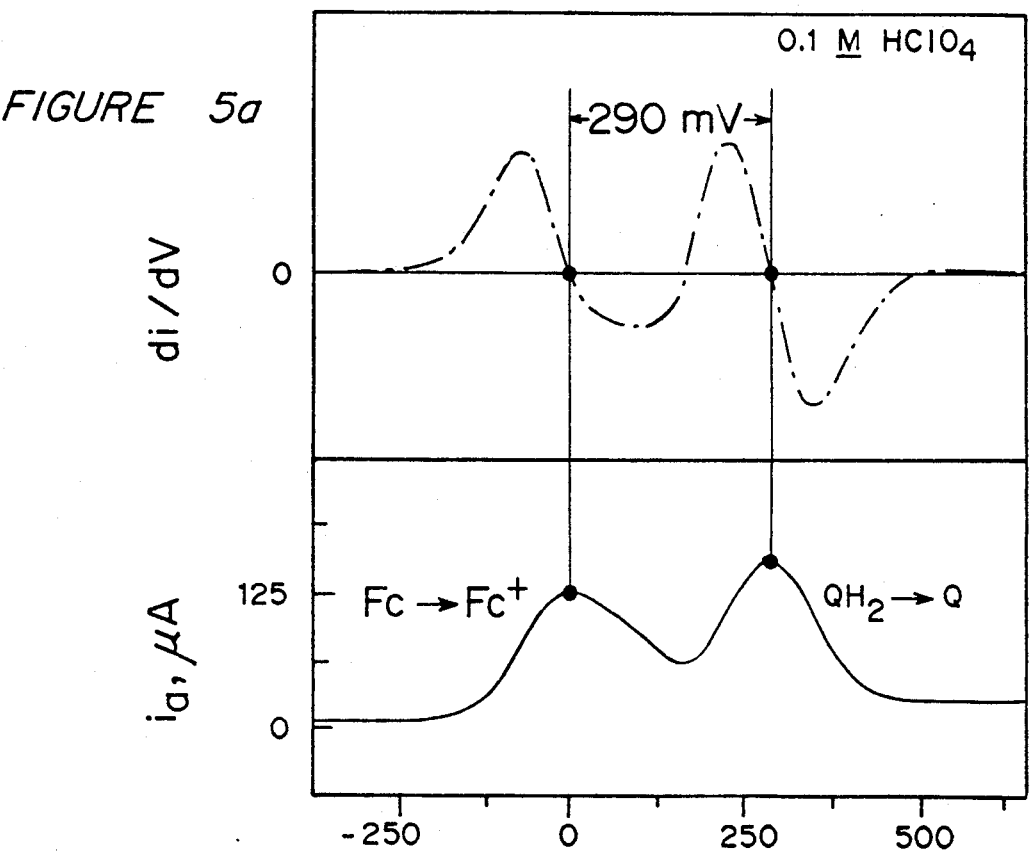
FIGS. 5A and 5B are linear sweep voltammograms (500 mV/s) and their first derivatives for oxidation of alkyl ferrocene thiol and hydroquinone thiol confined to an Au macroelectrode, in 0.1 M $HClO_4$ (FIG. 5A) and in 3 M $HClO_4$ (FIG. 5B). The potential scale is relative to the Fc oxidation wave.
Figure 5B:
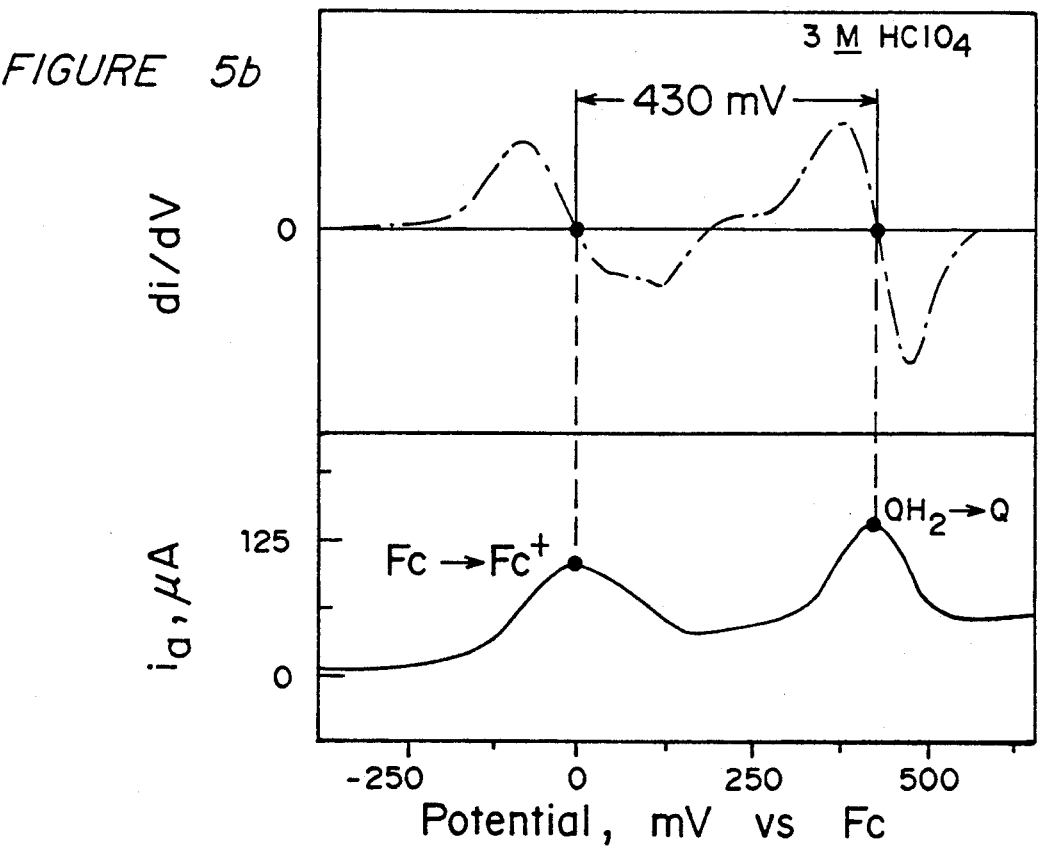

Linear sweep voltammograms at 500 mV/s and their first derivatives for oxidation of alkyl ferrocene thiol and hydroquinone thiol confined to a Au macroelectrode in either 0.1 M $HClO_4$ or 3 M $HClO_4$, on a scale relative to the Fc oxidation wave, shown in FIG. 5, demonstrate the use of the derivatives to establish the differences in the peak positions for the oxidation of the ferrocene and the hydroquinone centers confined to a Au electrode.

The derivative mode for locating peak positions lends itself particularly well to the interfacing of the sensor with electronic instrumentation. The zeros of a derivative are easily identified electronically, and at a given linear voltammetric sweep rate, clock time between zeros will correspond to a give delta E or separation between reference and indicator current peaks.

EXAMPLE 4:

Construction of a Surface Confined Two-terminal CO Sensor.

Self-assembly of ferrocenyl ferraazetine disulfide and a ferrocenyl dithiol onto an Au microelectrode was used to demonstrate a two terminal microsensor for CO. The reference molecule, ferrocenyl dithiol, is a redox molecule having a chemically insensitive formal potential. The indicator molecule is ferrocenyl ferraazetine disulfide which has a CO dependent formal potential. Au micro- or macroelectrodes can be modified with the above reference or indicator molecules by dipping the Au electrodes into solutions containing one or both of the compounds. Ferrocenyl ferraazetine disulfide was synthesized according to the following scheme:

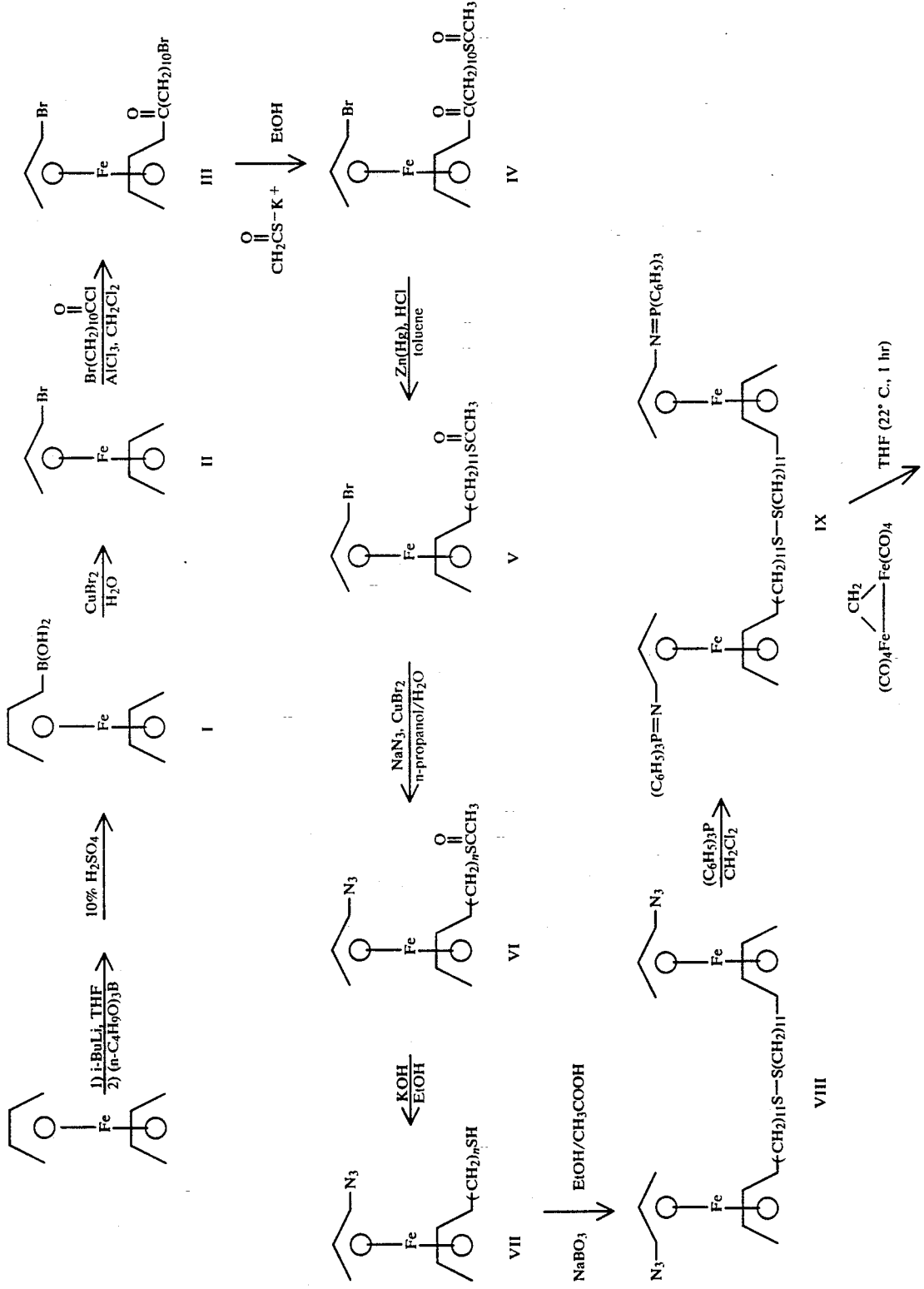

-continued
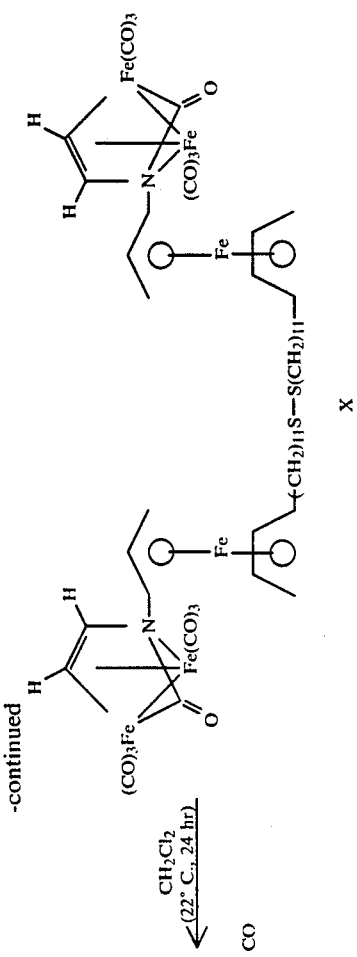
X
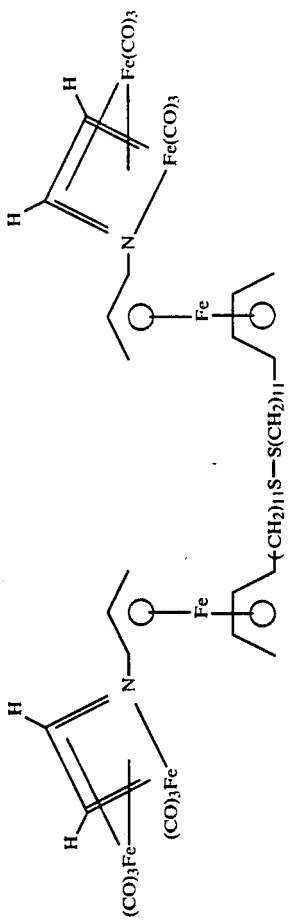
XI

Figure 6A:
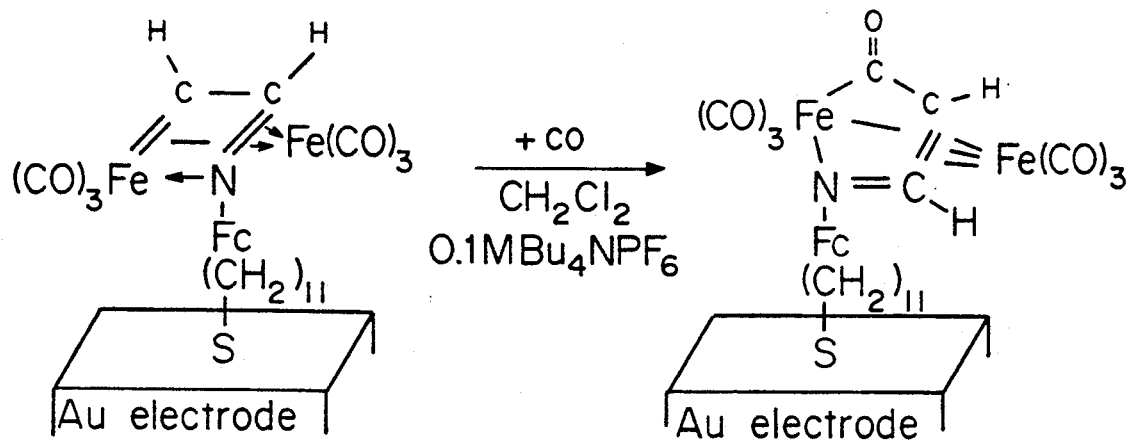
FIG. 6A illustrates a cross-sectional view of a two-terminal, voltammetric microsensor for CO formed using as the reference molecule, ferrocenyl dithiol, a redox molecule having a chemically insensitive formal potential, and ferrocenyl ferraazetine disulfide as the indicator molecule, a redox molecule having a CO dependent formal potential.
Figure 6B:
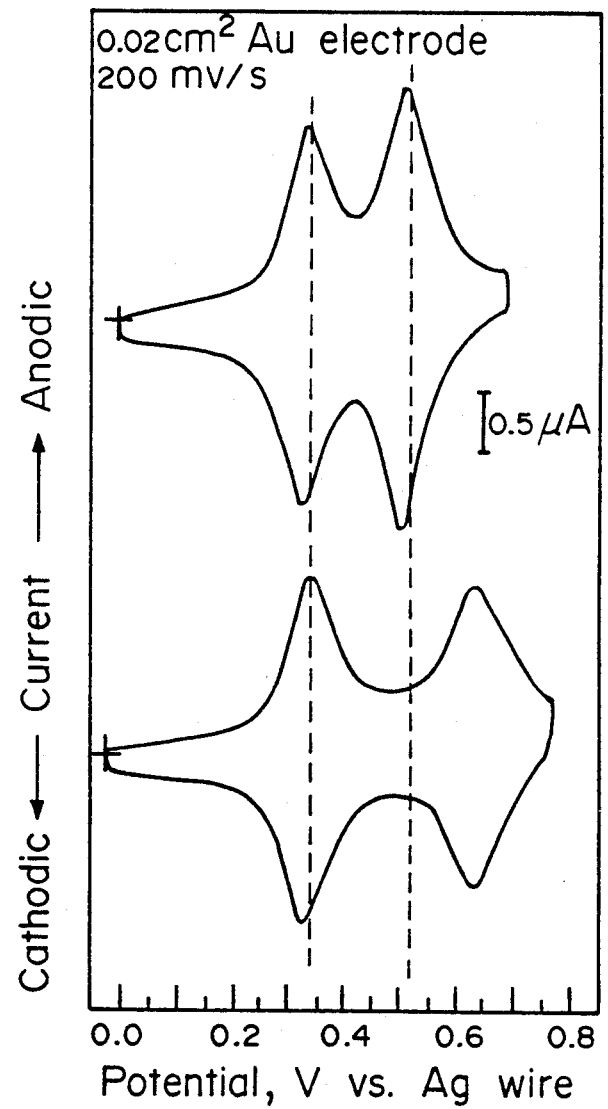
FIG. 6B is a linear sweep voltammogram where the reference wave (the wave at more negative potential) which is insensitive to CO remains constant in potential, while the indicator wave shifts 120 mV positive.

All materials were characterized by $^1$H NMR, FTIR, and Mass Spectrometry. Elemental analyses were consistent with the proposed structures. Self assembled monolayers of ferrocenyl ferraazetine disulfide were obtained by dipping Au electrodes into 1 mM ferrocenyl ferraazetine disulfide/hexane solutions. Subsequent exposure of the ferrocenyl ferraazetine disulfide treated electrodes to 1 mM hexane solutions of reference molecule, ferrocenyl dithiol, resulted in adsorption of the reference molecule onto the electrode surface. A 1:1 sensor:reference molecule surface coverage was achieved for a three minute exposure time, as shown in FIG. 6, demonstrating the CO dependent cyclic voltammetry of an Au macroelectrode (0.02 cm$^2$) modified as described. Upon exposure to CO, the reference wave (the wave at more negative potential) which is insensitive to CO remains constant in potential, whereas the indicator wave shifts 120 mV positive.

Preliminary studies indicate that a comparable effect may be observed with a microelectrode device operated as a two terminal device using a solid electrolyte such as poly[bis(2-(2'-methoxyethoxy)ethoxy) phosphazene] (MEEP)/LiCF$_3$SO. The latter demonstrates a two terminal solid state gas sensor for CO.

Au electrodes derivatized with thiol reagents are quite robust, but obviously long term durability is an issue in many sensor applications. Sensor electrodes described in examples 1 to 3 have been used intermittently over a period of several weeks with reproducible response to variation in pH. The two-terminal, voltammetric microsensor is self-assessing, in that failure of the device-active materials is revealed by an inability to detect current peaks.

Modifications and variations of the sensor devices and methods of preparation and use thereof will be obvious to those skilled in the art from the foregoing description. Such modifications and variations are intended to come within the scope of the appended claims.

We claim:

1. An two-terminal voltammetric electrochemical sensor comprising:
   a working, electrode comprising surface confined chemically sensitive redox material and chemically insensitive redox material in a thickness functionally equivalent to that of a monolayer, wherein the two materials act as terminals and
   a counterelectrode having a surface area at least 10$^2$ larger than the surface area of the working electrode.

2. The sensor of claim 1 further comprising means for measuring a difference in redox potential between the chemically sensitive redox material and the chemically insensitive redox material.

3. The sensor of claim 2 wherein the measuring means applies a linear sweep of applied voltage to the sensor and detects the difference in separations between changes in potential of the two redox materials.

4. The sensor of claim 1 wherein the conductivity of the chemically sensitive redox material changes in response to changes in pH and the conductivity of the chemically insensitive redox material does not measurably change in response to changes in pH.

5. The sensor of claim 1 comprising more than one different chemically sensitive redox materials.

6. The sensor of claim 1 wherein the electrode is formed on an inert, electrically conductive material selected from the group consisting of platinum, gold, silver, palladium, carbon, tin doped indium oxide, tin oxide and combinations thereof.

7. The sensor of claim 1 wherein the electrode is formed of an inert, electrically conductive material on a chemically inert, electrically insulating material.

8. The sensor of claim 1 wherein the redox materials are electroactive molecules with functional groups that bind or coordinate to the electrode surface.

9. The sensor of claim 1 wherein the redox materials bind or coordinate to another material confined to the electrode surface.

10. A method for making a two-terminal voltammetric sensor comprising
    forming a working electrode having a chemically sensitive redox material and a chemically insensitive redox material confined on the surface of an electrically conductive substrate in a thickness functionally equivalent to that of a monolayer, wherein the two materials act as terminals, and a counter electrode having a surface area at least 10$^2$ larger than the surface area of the working electrode.

11. The method of claim 10 further comprising placing the electrode in an environment where a change in chemical concentration is to be detected, applying means for measuring a difference in redox potential between the chemically sensitive redox material and the chemically insensitive redox material to the electrode, and measuring a difference in redox potential as a function of the change in chemical concentration at the electrode.

12. The method of claim 11 further wherein a linear sweep of voltage is applied to the sensor and the difference in separations between changes in potential of the two redox materials is measured.

13. The method of claim 10 wherein the conductivity of the chemically sensitive redox material changes in response to changes in pH and the conductivity of the chemically insensitive redox material does not measurably change in response to changes in pH, further comprising detecting changes in pH.

14. The method of claim 10 wherein the microelectrode comprises more than one different chemically sensitive redox materials, further comprising measuring changes in chemical concentration of more than one species.

* * * * *

UNITED STATES PATENT AND TRADEMARK OFFICE
CERTIFICATE OF CORRECTION

PATENT NO. : 5,223,117
DATED : June 29, 1993
INVENTOR(S) : Mark S. Wrighton, James J. Hickman, Paul E. Laibinis, David Ofer, Chad A. Mirkin, James Valentine, & George Whitesides It is certified that error appears in the above-indentified patent and that said Letters Patent is hereby corrected as shown below:

Column 1, line 9, add --This invention was also made with Government support under Contract N00014-86-K-0756 awarded by the Department of the Navy.-- after "Agency."

Column 2, line 21, replace "voltammemtric" with --voltammetric--.

Column 3, line 15, replace "FIGS." with --FIG.--.

Column 4, line 21, replace "bu" with --but--.

Column 4, line 34, replace "RuO.," with --$RuO_x$--.

Column 7, line 50, replace "Fc++e-" with --Fc + $e^-$--.

Signed and Sealed this

Twelfth Day of July, 1994

Attest:

BRUCE LEHMAN

*Attesting Officer*   Commissioner of Patents and Trademarks